United States Patent [19]
Elkins et al.

[11] 4,138,743
[45] Feb. 13, 1979

[54] LIQUID COOLED HELMET

[75] Inventors: William Elkins, San Jose; Bill A. Williams, Morgan Hill, both of Calif.

[73] Assignee: Acurex Corporation, Mountain View, Calif.

[21] Appl. No.: 749,970

[22] Filed: Dec. 13, 1976

Related U.S. Application Data

[63] Continuation of Ser. No. 553,030, Feb. 25, 1975, abandoned.

[51] Int. Cl.² .............................................. A42B 1/04
[52] U.S. Cl. ...................................... 2/171.2; 150/2.3; 2/202
[58] Field of Search ................ 2/171.2, 202, 203, 205, 2/2.1 R, 7, 68, 84; 128/403, 380; 150/2.3, 2.4

[56] References Cited
U.S. PATENT DOCUMENTS

| | | | |
|---|---|---|---|
| 2,403,676 | 7/1946 | Modlinski | 2/84 UX |
| 3,255,460 | 6/1966 | Pastore | 2/68 |
| 3,744,053 | 7/1973 | Parker et al. | 2/2.1 R |

OTHER PUBLICATIONS

Gershman, "Self Adhering Nylon Tapes", Oct. 18, 1958, J.A.M.A., vol. 68, No. 7, p. 930.

*Primary Examiner*—Werner H. Schroeder
*Assistant Examiner*—Peter Nerbun
*Attorney, Agent, or Firm*—Flehr, Hohbach, Test, Albritton & Herbert

[57] ABSTRACT

Liquid cooled helmet comprising a cap of flexible material adapted to fit the head of a person, cooling panels mounted inside the cap forming passageways for carrying a liquid coolant, the panels being positioned to engage the cranium and neck of a person wearing the helmet, inlet and outlet lines communicating with the passageways, and releasable straps for securing the helmet about the neck of the wearer.

5 Claims, 3 Drawing Figures

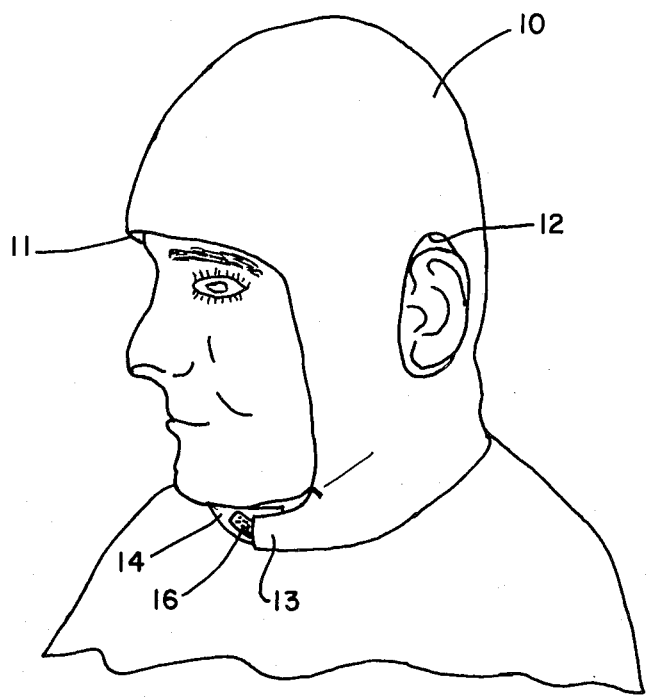
FIG.—1
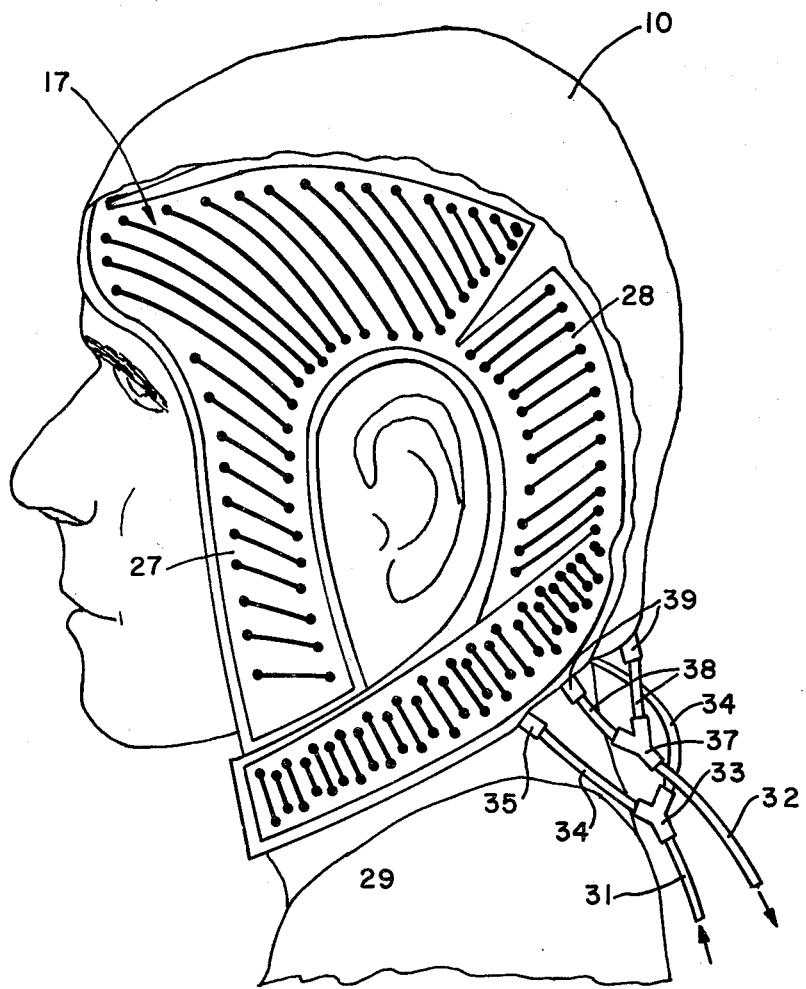
FIG.—2

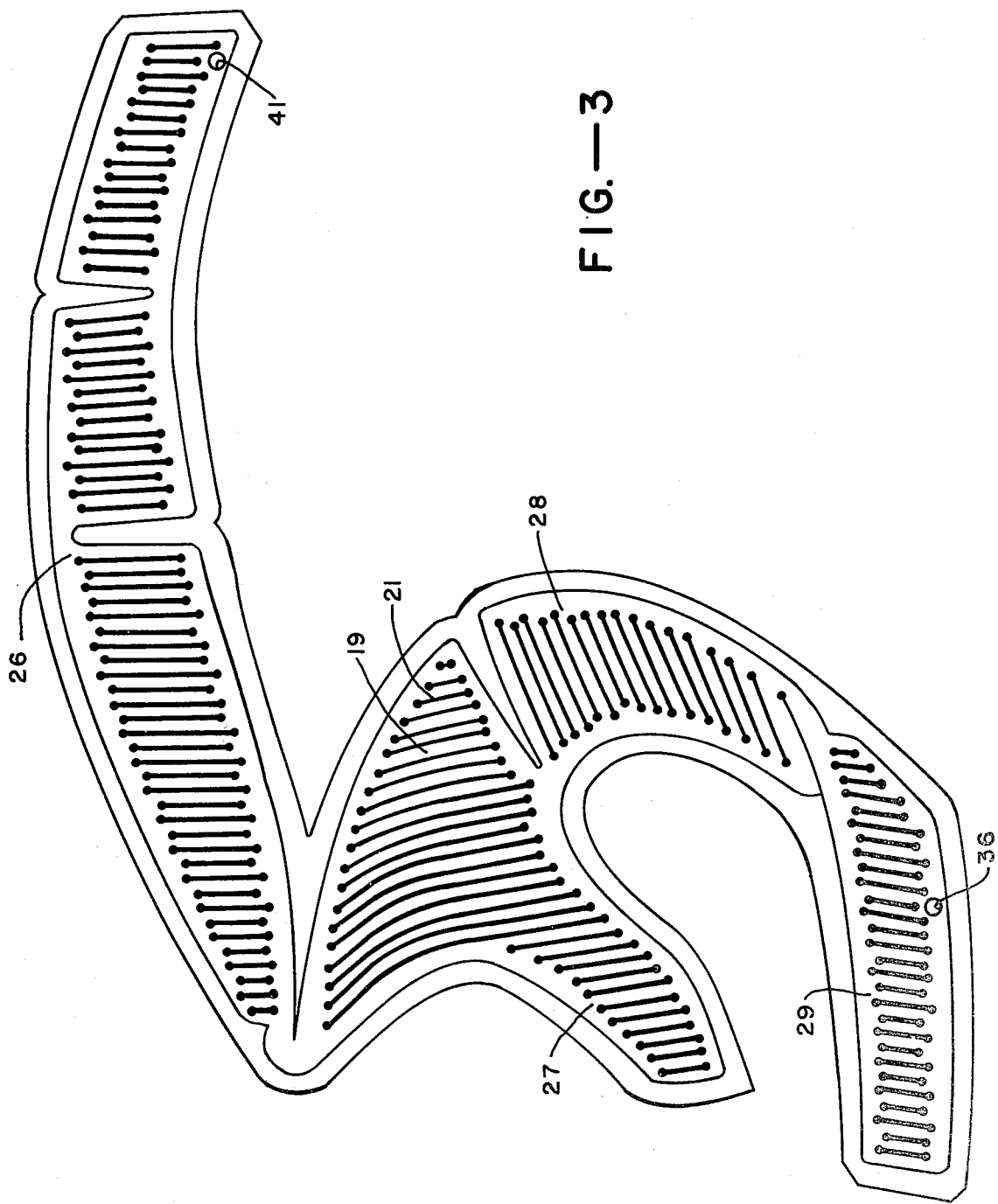
FIG.—3

LIQUID COOLED HELMET

The invention described herein was made in the performance of work under NASA Contract Number NAS2-6650 and is subject to the provisions of Section 305 of the National Aeronautics and Space Act of 1958 (72 Stat. 435; 42 U.S.C. 2457).

This is a continuation of application Ser. No. 553,030 filed Feb. 25, 1975, now abandoned.

BACKGROUND OF THE INVENTION

This invention pertains generally to devices for cooling the human body and more particularly to a liquid cooled helmet for cooling the head and neck of a wearer.

The invention was made in the course of Contract No. NAS2-6650 with the United States of America as represented by the National Aeronautics and Space Administration.

Heretofore, devices utilizing a circulating liquid have been provided for cooling different parts of the body. One such device is described in U.S. Pat. No. 3,830,676, issued Aug. 20, 1974 to the assignee herein.

Cooling of the head has been found to be particularily advantageous. For example, through experimentation and testing, it has been found that a considerable degree of comfort is provided to persons in warm environments, such as race car drivers, by cooling the head and neck. In addition, it appears that cooling the head may retard or even prevent the loss of hair heretofore experienced by persons undergoing chemotherapy.

SUMMARY AND BACKGROUND OF THE INVENTION

The invention provides a liquid cooled helmet comprising a cap of flexible material adapted to fit the head of a person, cooling panels mounted inside the cap forming passageways for carrying a liquid coolant, said panels being positioned to engage the cranium and neck of a person wearing the helmet, inlet and outlet lines communicating with the passageways, and releasable cap means for securing the helmet about the neck of the wearer.

It is in general an object of the invention to provide a liquid cooled helmet of the above character which is lightweight and flexible and therefore comfortable to wear.

Additional objects and features of the invention will be apparent from the following description in which the preferred embodiment is set forth in detail in conjunction with the accompanying drawings.

BRIEF DESCRIPTION OF THE DRAWINGS

FIG. 1 is a perspective view, illustrating a liquid cooled helmet according to the invention on the head of a person.

FIG. 2 is a fragmentary view of the helmet of FIG. 1.

FIG. 3 is a plan view of a cooling panel utilized as a liner in the helmet of FIG. 1.

DESCRIPTION OF THE PREFERRED EMBODIMENT

As illustrated, the liquid cooled helmet comprises a cap 10 fabricated of a flexible elastic material adapted to fit on the head of a person and cover the head and neck, with openings 11 and 12 for the face and ears. In the preferred embodiment, the cap is woven of nylon spardex fibers.

Straps 13 and 14 extend from the lower front portions of the cap and are releasably fastened together under the chin of the wearer to secure the cap on the head. In the preferred embodiment, the straps are provided with Velcro fasteners 16 which permit the straps to be readily adjusted, joined and released.

A liner consisting of a pair of flexible cooling panels 17 is mounted inside the cap and positioned to engage the cranium and neck of the wearer. The two panels are mounted side by side in the cap, and each is formed to include a plurality of flow passageways 19 for carrying a suitable coolant such as water. The panels are secured to the cap by suitable means such as sewing.

Each of the cooling panels 17 is fabricated of two superposed sheets of a flexible waterproof material such as polyurethane, rubber, synthetic rubber or a fabric coated with an elastomeric material, and the sheets are sealed together by suitable means such as vulcanizing or heat-sealing at their edges and along spaced apart lines 21 to form passageway 19. In the preferred embodiment, the sheets from which the panels are fabricated are generally planar, and the panels conform generally to the contour of the head when mounted in the cap and placed on the head. As best seen in FIG. 3, each panel includes a section 26 for engaging one side of the top and rear of the head, a section 27 for engaging the side of the head in front of the ear, a section 28 for engaging the side of the head behind the ear, and a section 29 for engaging the neck beneath the ear and jaw.

Flow lines connected to the cooling panels communicate with passageways 19 and provide means for circulating coolant through the passageways. These lines include an inlet line 31 and an outlet line 32. Inlet line 31 is connected to each of the panels by means of a Y-connector 33, short flow lines 34, and elbow connectors 35 mounted in openings 36 in the rear portion of section 29 in communication with passageways 19. Similarily, outlet line 32 is connected to each of the panels by means of a Y-connector 37, short flow lines 38, and elbows 39 mounted in openings 41 in the lower portion of section 26 in communication with the passageways. In the preferred embodiment, lines 31, 32, 34 and 38 are fabricated of a flexible material such as plastic tubing.

In operation and use, the helment is placed on the head of a person with the cooling panels against the cranium and neck. Straps 13 and 14 are secured about the neck by the Velcro fastener, an inlet line 31 is connected to a suitable source of coolant. Outlet line 32 can either be returned to the source for a recirculating system or lead to a suitable discharge area.

The invention has a number of important features and advantages. It provides efficient cooling of the head and neck, and the helmet is lightweight, flexible and comfortable to wear.

It is apparent from the foregoing that a new and improved liquid cooled helmet has been provided. While only the preferred embodiment has been described, as will be apparent to those familiar with the art, certain changes and modifications can be made without departing from the scope of the invention as defined by the following claims.

We claim:

1. In a method of making a liquid cooled helmet having an elastic cap adapted to fit on the head of a person and conform closely to the contour of the head, the steps of: superposing two flat sheets of flexible material having portions for covering predetermined portions of the head; joining the flat sheets together along a plurality of predetermined lines spaced inwardly from the sheet's periphery to form a liner having interconnecting flow passageways for carrying a liquid coolant; mounting the liner in the cap with the portions of the sheets in position for covering the portions of the head when the helmet is placed on the head; and connecting flow lines to the liner for carrying the coolant to and from the passageways.

2. A liquid cooled helment having an elastic cap adapted to fit on the head of a person and conform closely to the non-planar contour of the head, a flexible liner mounted inside the cap for engagement with the head and having a plurality of passageways for carrying a liquid coolant, and inlet and outlet flow lines connected to the liner and communicating with the passageways for carrying the coolant to and from said passageways, wherein the liner is formed by the steps of superposing two flat sheets of flexible material, joining the two sheets together along a plurality of lines spaced inwardly of the periphery of the sheets to form the passageways, forming the superposed sheets to the non-planar contour of the cap, and securing the superposed sheets to the cap in position to be pressed against the head by the cap when the helmet is placed on the head.

3. The liquid cooled helmet of claim 2 further including means affixed to the cap for releasably securing the same about the neck of the person.

4. The liquid cooled helmet of claim 3 wherein the means for securing the cap about the neck comprises a hood and pile fastener.

5. The liquid cooled helmet of claim 2 wherein the liner comprises a pair of cooling panels each having sections for engaging one side of the top and rear of the head, one side of the head in front of the ear, and one side of the head below the ear and jaw.

* * * * *